United States Patent [19]

Nelson

[11] 4,117,138

[45] Sep. 26, 1978

[54] PYRROLIDONECARBOXYLIC ACID THERAPEUTIC AGENTS

[75] Inventor: Albin J. Nelson, Ledyard, Conn.

[73] Assignee: Pfizer Inc., New York, N.Y.

[21] Appl. No.: 833,909

[22] Filed: Sep. 16, 1977

Related U.S. Application Data

[62] Division of Ser. No. 647,132, Jan. 7, 1976, Pat. No. 4,064,264.

[51] Int. Cl.$^2$ .................. A61K 31/44; A61K 31/455; C07D 213/44
[52] U.S. Cl. .................................... 424/263; 424/266; 260/295 L; 260/295.5 A
[58] Field of Search .... 260/295 L, 295 AM, 295.5 A; 424/263, 266

[56] References Cited

PUBLICATIONS

Chem. Abstracts, vol. 80, 1974, paragraph 82679 S.

Primary Examiner—Henry R. Jiles
Assistant Examiner—Cary Owens
Attorney, Agent, or Firm—Connolly and Hutz

[57] ABSTRACT

A series of novel N-(p-benzamido)-2-pyrrolidone-4-carboxylic acid compounds have been prepared by condensing the corresponding p-aminobenzamides with itaconic acid. These pyrrolidone compounds are useful in therapy as anti-ulcer agents. N-[N'-(n-Decyl)-4'benzamido]-2-pyrrolidone-4-carboxylic acid represents a preferred embodiment.

4 Claims, No Drawings

PYRROLIDONECARBOXYLIC ACID THERAPEUTIC AGENTS

CROSS REFERENCE TO RELATED APPLICATION

This application is a division of application Ser. No. 647,132 filed Jan. 7, 1976, and now is Pat. No. 4,064,264 filed Dec. 20, 1977.

BACKGROUND OF THE INVENTION

This invention relates to new and useful N-substituted pyrrolidonecarboxylic acid compounds of principal interest to those in the field of chemotherapy. More particularly, it is concerned with certain novel N-(p-benzamido)-2-pyrrolidone-4-carboxylic acid compounds, which are of especial value in view of their unique anti-ulcer properties.

In the past, various attempts have been made by numerous investigators in the field of organic medicinal chemistry to obtain new and useful anti-ulcer agents. For the most part, these efforts have involved the synthesis and testing of various new and heretofore unavailable organic compounds, particularly in the area of organic heterocyclic bases. For instance, C. A. Lipinski in U.S. Pat. No. 3,862,190 discloses various 4-amino-5-phenoxypyrimidine compounds useful for these purposes. However, in the search for still new and better or more improved anti-ulcer agents, little is known about the effect of acidic functional groups on compounds of this type and particularly, a carboxylic acid group attached to a heterocyclic ring moiety.

SUMMARY OF THE INVENTION

In accordance with the present invention, it has now been rather unexpectedly found that certain novel N-substituted pyrrolidonecarboxylic acid compounds are extremely useful when employed in therapy as anti-ulcer agents. More specifically, the novel compounds of this invention are all selected from the group consisting of N-(p-benzamido)-2-pyrrolidone-4-carboxylic acids of the formula:

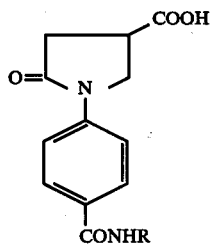

and the lower alkyl esters and unsubstituted amide derivatives thereof, and the base salts of said acids with pharmacologically acceptable cations, wherein R is a member selected from the group consisting of alkyl having from seven to eighteen carbon atoms arranged in a straight chain, benzyl, β-phenylethyl and 2-pyridyl. These novel compounds all possess anti-ulcer activity to a significantly high degree and are therefore useful in the treatment of peptic ulcers.

Of special interest in this connection are such typical and preferred members of the invention as N-[N'-(n-octyl)-4'-benzamido]-2-pyrrolidone-4-carboxylic acid, N-[N'-(n-nonyl)-4'-benzamido]-2-pyrrolidone-4-carboxylic acid, N-[N'-(n-decyl)-4'-benzamido]-2-pyrrolidone-4-carboxylic acid, N-[N'-(n-undecyl)-4'-benzamido]-2-pyrrolidone-4-carboxylic acid, N-[N'-(n-dodecyl)-4'-benzamido]-2-pyrrolidone-4-carboxylic acid and N-[N'-(2-pyridyl)-4'-benzamido]-2-pyrrolidone-4-carboxylic acid, respectively. These particular compounds are all highly potent as regards their anti-ulcer activity.

DETAILED DESCRIPTION OF THE INVENTION

In accordance with the process employed for preparing the novel compounds of this invention, an appropriate p-amino-N-(substituted)benazmide of the formula:

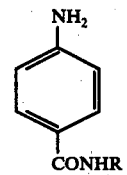

wherein R is defined as aforesaid, is condensed with itaconic acid to form the desired N-(p-benzamido)-2-pyrrolidone-4-carboxylic acid final product of the structural formula previously indicated. This particular reaction is normally conducted in the absence of a solvent by fusing the two reactants together at a temperature that is at least about equal to the boiling point of water, whereby the resultant water of reaction is substantially removed from the reaction mixture as quickly as it is formed. The reaction may also be conducted in the presence of a solvent such as benzene, toluene, n-hexane and methyl isobutyl ketone, etc. A preferred temperature for the reaction would be one that is normally in the range of from about 100° C. to about 140° C. for the present purposes at hand, i.e., until all the water of reaction has been substantially removed from the reaction mixture and this will usually require a period of at least about an hour. In general, substantially equimolar proportions of reactants are employed, although the ratio can vary anywhere from about 0.5 to about 2.0 moles of itaconic acid per mole of amine without causing unwanted side reactions to occur to any significant degree. Upon completion of the reaction, the desired product is easily isolated in a conventional manner, e.g., by first cooling the reaction mixture to room temperature and then dissolving same in dilute aqueous alkali, followed by filtration and subsequent acidification of the resulting filtrate to afford the particular N-(p-benzamido)-2-pyrrolidone-4-carboxylic acid in the form of a readily-recoverable precipitate.

The lower alkyl esters of the N-(p-benzamido)-2-pyrrolidone-4-carboxylic acids of this invention are generally prepared by condensation of the acid with the appropriate alcohol in the presence of an acid catalyst in accordance with conventional organic procedure. The unsubstituted amide derivatives, on the other hand, are readily prepared by using standard procedures, for example, by treating the corresponding acid chloride with ammonia under basic conditions and thereafter isolating the amide final product in the usual manner.

The starting materials required for preparing the novel N-(p-benzamido)-2-pyrrolidone-4-carboxylic acid compounds of this invention are either readily available commercially, like itaconic acid, or else they can easily be synthesized by those skilled in the art starting from common chemical reagents and using conventional methods of organic synthesis. For instance, the p-amino-N-alkylbenzamides are all readily prepared by reacting p-nitro-benzoyl chloride with the appropriate alkyl amine ($RNH_2$) and thereafter subjecting the resulting p-nitro-N-alkylbenzamide intermediate to catalytic hydrogenation in accordance with the general procedure of H. Wenker, as described in the *Journal of the American Chemical Society*, Vol. 60, p. 1081 (1938).

The chemical bases which are used as reagents in this invention to prepare the aforementioned pharmaceutically acceptable base salts are those which form non-toxic salts with various herein described N-(p-benzamido)-2-pyrrolidone-4-carboxylic acids, such as N-[N'-(n-decyl)-4'-benzamido]-2-pyrrolidone-4-carboxylic acid, for example. These particular non-toxic base salts are of such a nature that their cations are said to be essentially non-toxic in character over the wide range of dosage administered. Examples of such cations include those of sodium, potassium, calcium and magnesium, etc. These salts can easily be prepared by simply treating the aforementioned N-(p-benzamido)-2-pyrrolidone-4-carboxylic acids with an aqueous solution of the desired pharmacologically acceptable cation, and then evaporating the resulting solution to dryness while preferably being placed under reduced pressure. Alternatively, they may also be prepared by mixing lower alkanolic solutions of the said acidic compounds and the desired alkali metal alkoxide together, and then evaporating the resulting solution to dryness in the same manner as before. In either case, stoichiometric quantities of reagents must be employed in order to ensure completeness of reaction and maximum production of yields with respect to the desired final product.

As previously indicated, the N-(p-benzamido)-2-pyrrolidone-4-carboxylic acid compounds of this invention are all readily adapted to therapeutic use as anti-ulcer agents, especially in view of their ability to control peptic ulcer formation in stressed subjects to a statistically significant degree. For instance, N-[N'-(n-decyl)-4-benzamido]-2-pyrrolidone-4-carboxylic acid, a typical and preferred agent of the present invention, has been found to consistently control (i.e., inhibit) the formation of peptic ulcers in stressed rats to a significantly high degree when given by the intraperitoneal route of administration at dose levels ranging from 10 mg./kg. to 32 mg./kg., respectively, without showing any substantial signs of toxic side effects. The other compounds of this invention also cause similar results. Furthermore, all the herein described compounds of this invention can be administered orally, for the present purposes at hand, without causing any significant untoward pharmacological side reactions to occur in the subject to whom they are so administered. In general, those compounds are ordinarily administered at dosage levels ranging from about 1.0 mg. to about 25 mg. per kg. of body weight per day, although variations will necessarily occur depending upon the condition and individual response of the subject being treated and the particular type of pharmaceutical formulation chosen.

In connection with the use of the N-(p-benzamido)-2-pyrrolidone-4-carboxylic acid compounds of this invention for the treatment of subjects afflicted with peptic ulcers, it is to be noted that they may be administered either alone or in combination with pharmaceutically acceptable carriers and that such administration can be carried out in both single and multiple dosages. More particular, the novel compounds of this invention can be administered in a wide variety of different dosage forms, i.e., they may be combined with various pharmaceutically acceptable inert carriers in the form of tablets, capsules, lozenges, troches, hard candies, powders, aqueous suspensions, elixirs, syrups and the like. Such carriers include solid diluents or fillers, sterile aqueous media and various non-toxic organic solvents, etc. Moreover, such standard pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as anti-ulcer agents, is determined by their ability to inhibit ulcer formation in cold-restraint stressed rats according to the procedure described by C. A. Lipinski in U.S. Pat. No. 3,862,190. The latter method essentially compares the median number of gastric erosions recorded in the control group with the median number of gastric erosions recorded in the drug-treated group and from this, the percent reduction in the total number of lesions can be readily calculated and reported as anti-ulcer activity per se. In this way, the N-(p-benzamido)-2-pyrrolidone-4-carboxylic acid compounds of this invention are shown to markedly control peptic ulcer formation in non-fasted rats when administered to them intraperitoneally at dose levels as low as 10 mg./kg. for the present purposes at hand.

PREPARATION A

To a stirred solution consisting of 15.73 g. (0.10 mole) of n-decylamine dissolved in 200 ml. of chloroform at room temperature (∼25° C), there were added 18.5 g. (0.10 mole of p-nitrobenzoyl chloride in the form of a solid material divided into separate small portions. Upon completion of this step, 250 ml. of 5% aqueous sodium hydroxide solution was rapidly added thereto and the resulting two-phase reaction mixture was then stirred overnight (∼16 hrs.) at room temperature and finally allowed to separate. The aqueous phase was next washed once with 200 ml. of chloroform and the chloroform washing added to the organic phase, while the combined organic solution was thereafter washed once with 300 ml. of a saturated aqueous sodium chloride solution and finally dried over anhydrous magnesium sulfate. After removal of the drying agent by means of suction filtration and the chloroform solvent by means of evaporation under reduced pressure, there was obtained a crude solid residue which subsequently gave 20.82 g. (95%) of pure p-nitro-N-(n-decyl)benzamide (m.p. 88°–90° C.) on recrystallization from a minimum amount of chloroform and methanol.

PREPARATION B

The procedure described in Preparation A was repeated to prepare the following p-nitro-N-alkylbenzamides, using an equivalent amount in moles of the appropriate monoalkylamine compound as the reagent in each instance:
p-nitro-N-(n-octyl)benzamide, m.p. 82°–84° C.
p-nitro-N-(n-nonyl)benzamide, m.p. 79°–81° C.
p-nitro-N-(n-undecyl)benzamide, m.p. 88°–89° C.
p-nitro-N-(n-dodecyl)benzamide, m.p. 93°–94° C.
p-nitro-N-(n-tridecyl)benzamide, m.p. 85°–86° C.
p-nitro-N-(n-pentadecyl)benzamide, m.p. 95°–96° C.
p-nitro-N-(n-hexadecyl)benzamide, m.p. 96°–99° C.

PREPARATION C

The procedure described in Preparation A is repeated except that n-octadecylamino is the reagent of choice employed in lieu of n-decylamine and p-nitro-N-(n-octadecyl)benzamide is the corresponding final product thus obtained.

In like manner, the use of n-heptylamine as reagent in this reaction affords p-nitro-N-(n-heptyl)benzamide as the corresponding final product which is obtained.

PREPARATION D

The procedure described in Preparation A is repeated except that benzylamine is the reagent of choice employed in lieu of n-decylamine and p-nitro-N-benzylbenzamide is the corresponding final product thus obtained.

In like manner, the use of β-phenylethylamine as reagent in this reaction affords p-nitro-N-(β-phenylethyl)benzamide as the corresponding final product which is obtained.

PREPARATION E

A slurry of 29.00 g. (0.095 mole) of p-nitro-N-(n-decyl)-benzamide in 200 ml. of methanol contained in a Parr shaker bottle was warmed slightly to dissolve all the benzamide. Adams platinum oxide catalyst (0.1 g.) was then added and the mixture placed on a Parr hydrogen reduction apparatus and shaken until no further hydrogen uptake could be detected (27.0 lb. of hydrogen were absorbed over a period of 0.67 hrs.). The resultant slurry was next removed from the reaction vessel and subsequently dissolved in 250 ml. of hot methanol, followed by filtration through kieselguhr (infusorial earth) to remove the catalyst and a small amount of unidentified material that was insoluble in the hot methanol. The alcoholic filtrate was then concentrated in vacuo and there was ultimately obtained a crude solid material which after recrystallization from a minimum amount of methanol gave 22.0 g. (82%) of pure p-amino-N-(n-decyl)benzamide, m.p. 114°–117° C.

Anal. Calcd. for $C_{17}H_{28}N_2O$: C, 73.76; H, 10.21; N, 10.14. Found: C, 74.03; H, 9.94; N, 10.27.

PREPARATION F

The procedure described in Preparation E was used to prepare the following p-amino-N-alkylbenzamides, starting from the corresponding p-nitro-N-alkylbenzamide compound of Preparation B in each instance:
p-amino-N-(n-octyl)benzamide, m.p. 118°–120° C.
p-amino-N-(n-nonyl)benzamide, m.p. 111°–114° C.
p-amino-N-(n-undecyl)benzamide, m.p. 115°–117° C.
p-amino-N-(n-dodecyl)benzamide, m.p. 121°–122° C.
p-amino-N-(n-tridecyl)benzamide, m.p. 120°–121° C.
p-amino-N-(n-pentadecyl)benzamide, m.p. 117°–119° C.
p-amino-N-(n-hexadecyl)benzamide, m.p. 117°–120° C.

PREPARATION G

The procedure described in Preparation E is repeated except that p-nitro-N-(n-octadecyl)benzamide is the starting material employed in place of p-nitro-N-(n-decyl)benzamide and p-amino-N-(n-octadecyl)benzamide is the corresponding final product thus obtained.

In like manner, when p-nitro-(n-heptyl)benzamide is the starting material employed in this reaction, the corresponding final product obtained is p-amino-N-(n-heptyl)benzamide.

PREPARATION H

The procedure described in Preparation E is repeated except that p-nitro-N-benzylbenzamide is the starting material employed in place of p-nitro-N-(n-decyl)benzamide and p-amino-N-benzylbenzamide is the corresponding final product thus obtained.

In like manner, when p-nitro-N-(β-phenylethyl)benzamide is the starting material employed in this reaction, the corresponding final product obtained is p-amino-N-(β-phenylethyl)benzamide.

EXAMPLE I

An intimate mixture of 22.0 g. (0.795 mole) of p-amino-N-(n-decyl)benzamide and 10.34 g. (0.0795 mole) of itaconic acid was prepared by combining said materials together in a suitable round-bottomed flask with the aid of a magnetic stirring apparatus. The mixture was then heated via an oil bath to a temperature of ca. 130° C., while being maintained in a nitrogen atmosphere with continued stirring. At this point, the contents of the flask had completely turned to a liquid. After maintaining the bath temperature at 135° C. for a period of 0.6 hours, the material started to solidify again and was completely solid after an additional one-half hour at this same temperature. The sample was then cooled to room temperature (~25° C.) and dissolved in 250 ml. of cold 0.5 N aqueous sodium hydroxide solution, followed by filtration to remove any insoluble material present. The resulting filtrate was then adjusted to pH 3.0 with 6 N hydrochloric acid, while being maintained at 0° C. throughout this step by means of immersion in an ice bath. The precipitate which soon formed was filtered and thereafter washed with cold water and air-dried. Recrystallization of the crude material from absolute ethanol then gave 20.18 g. (67%) of pure N-[N'-(n-decyl)-4'-benzamido]-2-pyrrolidone-4-carboxylic acid, m.p. 174°–177° C.

Anal. Calcd. for $C_{22}H_{32}N_2O_4$: C, 68.01; H, 8.30; N, 7.21. Found: C, 68.14; H, 8.46; N, 7.40.

EXAMPLE II

The procedure described in Example I was repeated except that p-amino-N-(n-octyl)benzamide was the starting material employed in place of p-amino-N-(n-decyl)benzamide, using the same molar proportions as before. In this particular case, the corresponding final product obtained was N-[N'-(n-octyl)-4'-benzamido]-2-pyrrolidone-4-carboxylic acid, m.p. 175°–177° C.

Anal. Calcd. for $C_{20}H_{28}N_2O_4$: C, 68.35; H, 7.74; N, 7.97. Found: C, 68.09; H, 7.88; N, 8.51.

EXAMPLE III

The procedure described in Example I was repeated except that p-amino-N-(n-nonyl)benzamide was the starting material employed in place of p-amino-N-(n-decyl)benzamide, using the same molar proportions as before. In this particular case, the corresponding final product obtained was N-[N'-(n-nonyl)-4'-benzamido]-2-pyrrolidone-4-carboxylic acid, m.p. 175°–178° C.

Anal. Calcd. for $C_{21}H_{30}N_2O_4$: C, 67.35; H, 8.08; N, 7.48. Found: C, 67.46; H, 8.00; N, 7.45.

EXAMPLE IV

The procedure described in Example I was repeated except that p-amino-N-(n-undecyl)benzamide was the starting material employed in place of p-amino-N-(n-decyl)benzamide, using the same molar proportions as before. In this particular case, the corresponding final product obtained was N-[N'-(n-undecyl)-4'-benzamido]-2-pyrrolidone-4-carboxylic acid, m.p. 178°–180° C.

Anal. Calcd. for $C_{23}H_{34}N_2O_4$: C, 68.63; H, 8.51; N, 6.96. Found: C, 68.87; H, 8.47; N, 7.02.

EXAMPLE V

The procedure described in Example I was repeated except that p-amino-N-(n-dodecyl)benzamide was the starting material employed in place of p-amino-N-(n-decyl)benzamide, using the same molar proportions as before. In this particular case, the corresponding final product obtained was N[N'-(n-dodecyl)-4'-benzamido]-2-pyrrolidone-4-carboxylic acid, m.p. 177°–183° C.

Anal. Calcd. for $C_{24}H_{36}N_2O_4$: C, 69.20; H, 8.71; N 6.73. Found: C, 69.57; H, 8.65; N, 6.75.

EXAMPLE VI

The procedure described in Example I was repeated except that p-amino-N-(n-tridecyl)benzamide was the starting material employed in place of p-amino-N-(n-decyl)benzamide, using the same molar proportions as before. In this particular case, the corresponding final product obtained was N-[N'-(n-tridecyl)-4'-benzamido]-2-pyrrolidone-4-carboxylic acid, m.p. 179°–181° C.

Anal. Calcd. for $C_{25}H_{38}N_2O_4$: C, 69.73; H, 8.90; N, 6.41. Found: C, 70.50; H, 9.08; N, 6.41.

EXAMPLE VII

The procedure described in Example I was repeated except that p-amino-N-(n-pentadecyl)benzamide was the starting material employed in place of p-amino-N-(n-decyl)benzamide, using the same molar proportions as before. In this particular case, the corresponding final product obtained was N-[N'-(n-pentadecyl)-4'-benzamido]-2-pyrrolidone-4-carboxylic acid, m.p. 218°–220° C.

Anal. Calcd. for $C_{27}H_{42}N_2O_4$: C, 70.71; H, 9.23; N, 6.11. Found: C, 70.86; H, 9.32; N, 6.06.

EXAMPLE VIII

The procedure described in Example I was repeated except that p-amino-N-(n-hexadecyl)benzamide was the starting material employed in place of p-amino-N-(n-decyl)benzamide, using the same molar proportions as before. In this particular case, the corresponding final product obtained was N-[N'-(n-hexadecyl)-4'-benzamido]-2-pyrrolidone-4-carboxylic acid, m.p. 160°–163° C.

Anal. Calcd. for $C_{28}H_{44}N_2O_4$: C, 71.15; H, 9.38; N, 5.93. Found: C, 70.90; H, 9.24; N, 5.85.

EXAMPLE IX

The procedure described in Example I was repeated except that p-amino-N-(2-pyridyl)benzamide [R. B. Moffett et al., *Journal of Medicinal Chemistry*, Vol. 14. No. 10, p. 963 (1971)] was the starting material employed in place of p-amino-N-(n-decyl)benzamide, using the same molar proportions as before. In this particular case, the corresponding final product obtained was N-[N'-(2-pyridyl)-4'-benzamido]-2-pyrrolidone-4-carboxylic acid, m.p. 282.5°–282.5° C.

Anal. Calcd. for $C_{17}H_{15}N_3O_4$: C, 62.76; H, 4.65; N, 12.92. Found: C, 62.48; H, 4.84; N, 12.68.

EXAMPLE X

The procedure described in Example I is repeated except that p-amino-N-(3-pyridyl)benzamide is the starting material employed in place of p-amino-N-(n-decyl)benzamide, using the same molar proportions as before. In this particular case, the corresponding final product obtained is N-[N'-(3-pyridyl)-4'-benzamido]-2-pyrrolidone-4-carboxylic acid.

EXAMPLE XI

The procedure described in Example I is repeated except that p-amino-N-(4-pyridyl)benzamide is the starting material employed in place of p-amino-N-(n-decyl)benzamide, using the same molar proportions as before. In this particular case, the corresponding final product obtained is N-[N'-(4-pyridyl)-4'-benzamido]-2-pyrrolidone-4-carboxylic acid.

EXAMPLE XII

The procedure described in Example I is repeated except that p-amino-N-(n-octadecyl)benzamide is the starting material employed in place of p-amino-N-(n-decyl)benzamide, using the same molar proportions as before. In this particular case, the corresponding final product obtained is N-[N'-(n-octadecyl)-4'-benzamido]-2-pyrrolidone-4-carboxylic acid.

EXAMPLE XIII

The procedure described in Example I is repeated except that p-amino-N-(n-heptyl)benzamide is the starting material employed in place of p-amino-N-(n-decyl)-benzamide, using the same molar proportions as before. In this particular case, the corresponding final product obtained is N-[N'-(n-heptyl)-4'-benzamido]-2-pyrrolidone-4-carboxylic acid.

EXAMPLE XIV

The procedure described in Example I is repeated except that p-amino-N-benzylbenzamide is the starting material employed in place of p-amino-N-(n-decyl)benzamide, using the same molar proportions as before. In this particular case, the corresponding final product obtained is N-(N'-benzyl-4'-benzamido)-2-pyrrolidone-4-carboxylic acid.

EXAMPLE XV

The procedure described in Example I is repeated except that p-amino-N-(β-phenylethyl)benzamide is the starting material employed in place of p-amino-N-(n-decyl)benzamide, using the same molar proportions as before. In this particular case, the corresponding final prouct obtained is N-[N'-(β-phenylethyl)-4'-benzamido]-2-pyrrolidone-4-carboxylic acid.

EXAMPLE XVI

A solution consisting of 3.88 g. (0.01 mole) of N-[N'-(n-decyl)-4'-benzamido]-2-pyrrolidone-4-carboxylic acid dissolved in 100 ml. of ethanol is saturated with dry hydrogen chloride gas, and the resultant mixture is then refluxed for a period of approximately four hours. Upon completion of this step, the solvent is removed by means of evaporation under reduced pressure and the residue subsequently made alkaline by the addition thereto of a saturated aqueous sodium bicarbonate solution. The resulting solution is then extracted with diethyl ether, and the combined ethereal extracts are subsequently dried over anhydrous sodium sulfate and filtered. After removal of the drying agent by means of filtration and the solvent in the usual manner, there is obtained crude ester product in the form of a solid crystalline residue. Recrystallization of the latter material from ethanol-water then affords the pure ethyl ester of N-[N'-(n-decyl)-4'-benzamido]-2-pyrrolidone-4-carboxylic acid in substantial yield.

EXAMPLE XVII

The procedure described in Example XVI is repeated except that methanol is the reagent employed instead of ethanol and methyl N-[N'-(n-decyl)-4'-benzamido]-2-pyrrolidone-4-carboxylate is the corresponding final product thus obtained.

In like manner, the n-propyl, isopropyl, n-butyl, isobutyl, n-amyl, isoamyl and n-hexyl esters of N-[N'-(n-decyl)-4'-benzamido]-2-pyrrolidone-4-carboxylic acid are also similarly prepared by merely employing the appropriate alcohol in place of ethanol in each particular case.

EXAMPLE XVIII

The procedure described in Example XVI is repeated except that N-[N'-(2-pyridyl)--4'-benzamido]-2-pyrrolidone-4-carboxylic acid is the starting material employed in place of N-[N'-(n-decyl)-4'-benzamido]-2-pyrrolidone-4-carboxylic acid for the present purposes at hand. In this particular case, the corresponding final product thus obtained is the ethyl ester of N-[N'-(2-pyridyl)-4'-benzamido]-2-pyrrolidone-4-carboxylic acid.

In like manner, the methyl, n-propyl, isopropyl, n-butyl, isobutyl, n-amyl, isoamyl and n-hexyl esters of N-[N'-(2-pyridyl)-4'-benzamido]-2-pyrrolidone-4-carboxylic are also similarly prepared, as are the corresponding lower alkyl esters of the other N-(p-benzamido)-2-pyrrolidone-4-carboxylic acids of this invention which are reported in Examples II–VIII and X–XV, respectively.

EXAMPLE XIX

A mixture of 1.94 g. (0.005 mole) of N-[N'-(n-decyl)-4'-benzamido]-2-pyrrolidone-4-carboxylic acid and 10 ml. of thionyl chloride dissolved in 300 ml. of chloroform is refluxed for a period of 2.5-3.9 hours. After cooling to room temperature (~25° C.), the reaction mixture is slowly poured into a solution consisting of 4.5 g. of sodium hydroxide dissolved in 100 ml. of ammonium hydroxide. The resulting chloroform layer is then separated and subsequently evaporated to near dryness while under reduced pressure to give a residual solid. Recrystallization of the latter material from ethanol-water then yields pure N-[N'-(n-decyl)-4'-benzamido]-2-pyrrolidone-4-carboxamide in fine crystalline form.

EXAMPLE XX

The procedure described in Example XIX is repeated except that N-[N'-(2-pyridyl)-4'-benzamido]-2-pyrrolidone-4-carboxylic acid is the starting material employed in place of N-[N'-(n-decyl)-4'-benzamido]-2-pyrrolidone-4-carboxylic acid for the present purposes at hand. In this particular case, the corresponding final product thus obtained is N-[N'-(2-pyridyl)-4'-benzamido]-2-pyrrolidone-4-carboxamide.

In like manner, the unsubstituted amides of the other N-(p-benzamido)-2-pyrrolidone-4-carboxylic acids of this invention are also similarly prepared by merely employing the appropriate acid starting material (taken from Examples II–VIII and X–XV, respectively), in each particular case.

EXAMPLE XXI

The sodium salt of N-[N'-(n-decyl)-4'-benzamido]-2-pyrrolidone-4-carboxylic acid is prepared by dissolving said compound in water containing an equivalent amount in moles of sodium hydroxide and then freeze-drying the mixture. In this way, the desired alkali metal salt of the acid is obtained in the form of an amorphous powder which is freely soluble in water.

In like manner, the potassium and lithium salts are also similarly prepared, as are the alkali metal salts of all the other N-(p-benzamido)-2-pyrrolidone-4-carboxylic acids of this invention which are reported as Examples II–XV, respectively.

EXAMPLE XXII

The calcium salt of N-[N'-(n-decyl)-4'-benzamido]-2-pyrrolidone-4-carboxylic acid is prepared by dissolving said compound in water containing an equivalent amount of moles of calcium hydroxide and then freeze-drying the mixture. The corresponding magnesium salt is also prepared in like manner, as are all the other alkaline-earth metal salts not only of this particular compound, but also of those acids previously described in Examples II–XV, respectively.

EXAMPLE XXIII

A dry solid pharmaceutical composition is prepared by blending the following materials together in the proportions by weight specified below:

| | |
|---|---|
| N-[N'-(n-Decyl)-4'-benzamido]-2-pyrrolidone-4-carboxylic acid | 50 |
| Sodium citrate | 25 |
| Alginic acid | 10 |
| polyvinylpyrrolidone | 10 |
| Magnesium stearate | 5 |

After the dried composition is thoroughly blended, tablets are punched from the resulting mixture, each table being of such size that it contains 200 mg. of the active ingredient. Other tablets are also prepared in a similar fashion containing 25, 50 and 100 mg. of the active ingredient, respectively, by merely using the appropriate amount of the N-(p-benzamido)-2-pyrrolidone-4-carboxylic acid in each case.

EXAMPLE XXIV

A dry solid pharmaceutical composition is prepared by combining the following materials together in the proportions by weight indicated below:

| | |
|---|---|
| N-[N'-(2-Pyridyl) -4'-benzamido]-2-pyrrolidone-4-carboxylic acid | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE XXV

The N-(p-benzamido)-2-pyrrolidone-4-carboxylic acids of Examples I-IX were tested for antiulcer activity in groups of non-fasted female rats of the Charles River C-D strain, each rat weighing approximately 70-140 g. The rats were administered the test compound intraperitoneally (the compound was dissolved in saline solution containing 1% carboxymethylcellulose and 0.1% polysorbate 80) at dose levels of 32 mg./kg. and 100 mg./kg., respectively, three hours prior to being lightly anesthetized with diethyl ether and then taped in the supine position to individual sheets of acrylic plastic. Animals which received no test compound (carrier only) served as the control. Upon recovery from the anesthesia, all the restrained animals were positioned horizontally in a refrigerator at 10°-12° C. for a period of three hours and thereafter sacrificed by cervical dislocation. The abdomen of each rat that had been subjected to the aforesaid cold-restraint stress was then opened, the pylorus clamped and the stomach inflated with saline solution via an oral tube. Upon completion of this step, the esophagus was then clamped and the stomach thereafter excised for examination purposes. This was further facilitated by placing said organ in a 0.4% formaldehyde solution for approximately 30 seconds to harden the outer layers. Each stomach was then cut open along the greater curvature and the glandular portion examined for damage. The number of gastric erosions, their severity, plus the color of the stomach, all served as items to be recorded. The Mann-Whitney-Wilcoxon rank sum test was then used to compare the median number of gastric erosions in the control group with the median number of said erosions in each drug-treated group in order to determine if they are statistically different [E.g., see Dixon et al., "Introduction to Statistical Analysis," Third Edition, McGraw-Hill Book Company, New York, N.Y., pp. 344–347 (1969)]. On this basis, the present reduction in the total number of lesions (% R.T.L.) was calculated and reported as such (i.e., as antiulcer activity) for the various compounds listed in the table below:

| | Antiulcer Activity (% R.T.L.) | |
|---|---|---|
| Compound | 10 mg./kg. | 32 mg./kg. |
| Product of Example I | 60 | 80 |
| Product of Example II | 55 | 25 |
| Product of Example III | 91 | 85 |
| Product of Example IV | 34 | 68 |
| Product of Example V | 65 | 46 |
| Product of Example VI | 34 | 62 |
| Product of Example VII | — | 43 |
| Product of Example VIII | 63 | 56 |
| Product of Example IX | 69 | 32 |

What is claimed is:

1. A compound selected from the group consisting of N-[N'-(2-pyridyl)-4'-benzamido]-2-pyrrolidone-4-carboxylic acid, a lower alkyl ester or unsubstituted amide derivative thereof, and a base salt of said acid with a pharmacologically acceptable cation.

2. The N-[N'-(2-pyridyl)-4'-benzamido]-2-pyrrolidone-4-carboxylic acid compound of claim 1.

3. A method for combatting peptic ulcers in the treatment of a subject afflicted with said condition, which comprises administering to said subject a therapeutically-effective amount of a compound of claim 1.

4. The method of claim 3 wherein the compound administered is N-[N'-(2-pyridyl)-4'-benzamido]-2-pyrrolidone-4-carboxylic acid.

* * * * *